United States Patent
Hsieh

(10) Patent No.: US 10,246,396 B1
(45) Date of Patent: Apr. 2, 2019

(54) VANILLIN HAVING TETRAMER STRUCTURE

(71) Applicant: Tian-Jye Hsieh, Neipu Township (TW)

(72) Inventor: Tian-Jye Hsieh, Neipu Township (TW)

(*) Notice: Subject to any disclaimer, the term of this patent is extended or adjusted under 35 U.S.C. 154(b) by 0 days.

(21) Appl. No.: 15/943,977

(22) Filed: Apr. 3, 2018

(51) Int. Cl.
*C07C 47/58* (2006.01)
*G01N 23/00* (2006.01)
*G01N 23/20* (2018.01)
*G01N 24/08* (2006.01)
*G06F 19/00* (2018.01)

(52) U.S. Cl.
CPC ........ *C07C 47/58* (2013.01); *G01N 23/20075* (2013.01); *G01N 24/087* (2013.01); *G06F 19/701* (2013.01)

(58) Field of Classification Search
CPC .................................................. C07C 47/58
See application file for complete search history.

(56) References Cited

U.S. PATENT DOCUMENTS

| | | | |
|---|---|---|---|
| 6,670,390 B1* | 12/2003 | Romanczyk, Jr. | A23G 1/32 426/631 |
| 2015/0328274 A1* | 11/2015 | Kappagoda | A61K 36/87 424/766 |

* cited by examiner

*Primary Examiner* — Sikarl A Witherspoon
(74) *Attorney, Agent, or Firm* — Rosenberg, Klein & Lee

(57) ABSTRACT

A vanillin having a tetramer structure is revealed, comprising a first monomer, a second monomer, a third monomer, and a fourth monomer. Each of the monomers is constituted by $C_8H_8O_3$. The vanillin includes a first intermolecular hydrogen bond between the first monomer and the fourth monomer, and a second intermolecular hydrogen bond between the second monomer and the third monomer to stabilize the tetramer structure.

4 Claims, 3 Drawing Sheets

VANILLIN HAVING TETRAMER STRUCTURE

BACKGROUND OF THE INVENTION

1. Field of the Invention

The present invention relates to a vanillin having a tetramer structure, wherein the vanillin is constituted by four $C_8H_8O_3$ monomers and includes two intermolecular hydrogen bonds for stabilizing its structure according to X-ray crystallography.

2. Description of Related Art

*Neolitsea acuminatissima*, is a small evergreen tree endemic in Taiwan, and it occurs in natural broadleaf evergreen forests. *Neolitsea* genus (Lauraceae) is reported to possess various bioactivities. Accordingly, the activity compound, vanillin, can be extracted from *N. acuminatissima* to be applied to various fields, so as to increase the practicality and efficiency.

Vanillin (4-hydroxy-3-methoxybenzaldehyde) is a compound with a pleasant odor and used in the flavoring of many foods such as ice cream and bakery products. It has consistently proved to be an antimutagen, an anticlastogen, and an anticarcinogen for a variety of chemical and physical agents. However, the active ingredients and vanillin in most plants usually displayed as a monomeric form. The present inventors have isolated a vanillin from *N. acuminatissima* extract, and they found that the vanillin display a tetramer structure after further analyzing its structure.

SUMMARY OF THE INVENTION

In view of the above-mentioned problems, the object of the present invention is to provide a vanillin having a tetramer structure, wherein the vanillin is constituted by four $C_8H_8O_3$ monomers and includes two intermolecular hydrogen bonds for stabilizing its structure according to X-ray crystallography.

Disclosed herein is a vanillin having a tetramer structure, comprising a first monomer, a second monomer, a third monomer, a fourth monomer, a first intermolecular hydrogen bond between the first monomer and the fourth monomer, and a second intermolecular hydrogen bond between the second monomer and the third monomer; wherein the vanillin is isolated from *N. acuminatissima*, and each of the monomers is constituted by $C_8H_8O_3$. The first intermolecular hydrogen bond having a bonding length of 1.875 Å is formed between an oxygen atom of a methoxy group of the first monomer and a hydrogen atom of a hydroxyl group of the fourth monomer, and the second intermolecular hydrogen bond having a bonding length of 1.818 Å is formed between an oxygen atom of a methoxy group of the third monomer and a hydrogen atom of a hydroxyl group of the second monomer.

According to an embodiment of the present invention, the vanillin has characteristics of (i) $^1H$ NMR ($CDCl_3$) δ: 3.95 (3H, s, $C_3$—$OCH_3$), 6.20 (1H, br s, OH), 7.09 (1H, d, J=8.0 Hz, H-5), 7.30 (1H, d, J=2.0 Hz, H-2), 7.42 (1H, dd, J=8.0, 2.0 Hz, H-6), 9.76 (1H, s, CHO); and (ii) at 295 K, unit cell dimensions: a=14.0368(9) Å, b=7.8583(5) Å, c=14.9937(9) Å, α=90°, β=115.446(1)°, γ=90°, space group=P2(1), volume=1493.19(16) Å$^3$, Z=8, and $D_{calc}$=1.354 Mg/m$^3$.

DETAILED DESCRIPTION OF THE PREFERRED EMBODIMENT

Figure 1:
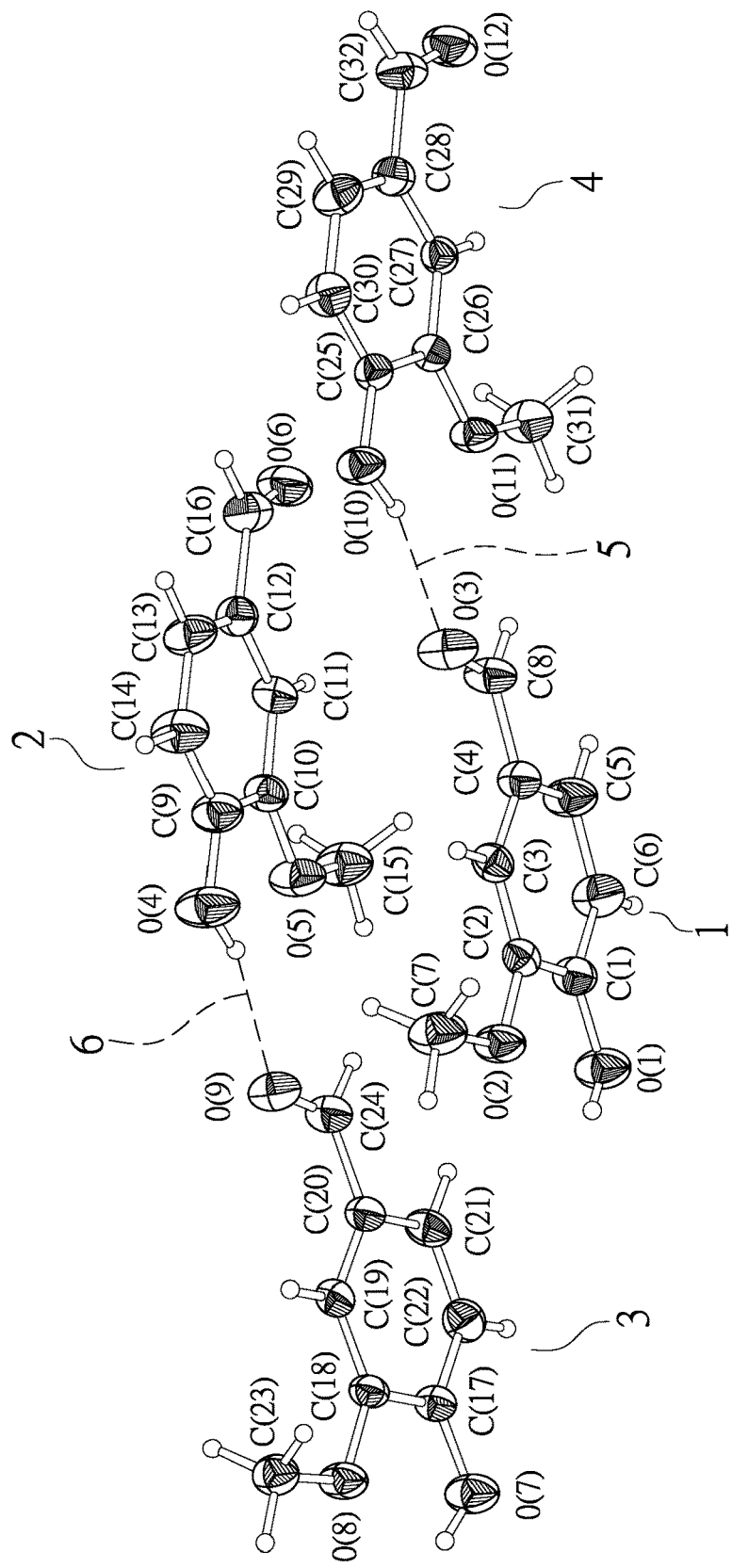
FIG. 1 is an ORTEP drawing of a vanillin according to the present invention.

A vanillin having a tetramer structure is disclosed. The vanillin as shown in FIG. 1 is isolated from the stems of *N. acuminatissima* and comprises a first monomer (1), a second monomer (2), a third monomer (3), a fourth monomer (4), a first intermolecular hydrogen bond (5) (bonding length=1.875 Å) between the first monomer (1) and the fourth monomer (4), and a second intermolecular hydrogen bond (6) (bonding length=1.818 Å) between the second monomer (2) and the third monomer (3), and wherein Each of the monomers is constituted by $C_8H_8O_3$ as shown in formula (I).

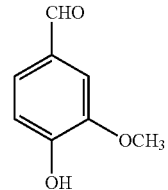 [SMILES: COc1cc(C=O)ccc1O]

Furthermore, the vanillin has characteristics of:

(i) $^1H$ NMR ($CDCl_3$) δ: 3.95 (3H, s, $C_3$—$OCH_3$), 6.20 (1H, br s, OH), 7.09 (1H, d, J=8.0 Hz, H-5), 7.30 (1H, d, J=2.0 Hz, H-2), 7.42 (1H, dd, J=8.0, 2.0 Hz, H-6), 9.76 (1H, s, CHO); and (ii) at 295 K, unit cell dimensions: a=14.0368(9) Å, b=7.8583(5) Å, c=14.9937(9) Å, α=90°, β=115.446(1)°, γ=90°, space group=P2(1), volume=1493.19(16) Å$^3$, Z=8, and $D_{calc}$=1.354 Mg/m$^3$.

Hereinafter, an exemplary embodiment of the present invention will be described in detail with reference to the accompanying drawings.

Example 1

First, a vanillin was isolated from the stems of *N. acuminatissima*, and its stereo-chemical structure was further determined by X-ray crystallography.

(a) Extraction and Isolation of Vanillin and Neolitacumone B

The stems (4.0 Kg) of *N. acuminatissima* were extracted repeatedly with MeOH at room temperature. The combined MeOH extracts were then evaporated and partitioned to yield $CHCl_3$ and aqueous extracts. The $CHCl_3$ extract was dried and evaporated to leave a viscous residue. The viscous residue was placed on a silica gel column and eluted with $CHCl_3$ gradually enriched with MeOH to afford 15 fractions.

Fraction 8 was purified by silica gel chromatography ($CHCl_3$/MeOH 10:3) to get vanillin (38.0 mg) as a compound of formula (I).

The isolated and vanillin respectively have characteristics as the followings.

Vanillin: $^1H$-NMR (CDCl3) δ: 3.95 (3H, s, C3-OCH3), 6.20 (1H, br s, OH), 7.09 (1H, d, J=8.0 Hz, H-5), 7.30 (1H, d, J=2.0 Hz, H-2), 7.42 (1H, dd, J=8.0, 2.0 Hz, H-6), 9.76 (1H, s, CHO).

The structure of molecules plays an especially significant role in determining their chemical properties. Only a slight change in the structure of a biological molecule can completely destroy its usefulness to a cell or may even change the cell from a normal one to cancerous one. As a result, to search the geometric optimization of compound is particularly important.

(b) Production of Single Crystal

Single crystal of vanillin was obtained by recrystallization followed by a crystal-growing process. Ethyl acetate was then slowly added to the mixture until the compound was completely dissolved. Vanillin was recrystallized in MeOH. Magnesium sulfate was then added, and the mixture was filtered while hot. The filtered product was then put into a crystal-growing bottle. Methanol vapor was allowed to slowly diffuse into the crystal-growing bottle until a perfect crystal was produced. The structure of the resulting single crystals was then analyzed by X-ray crystallography. Suitable crystals were selected, and then mounted on thin glass fibers using viscous oil. All measurements were made on a SMART CCD diffract meter with Mo Kα radiation ($\lambda$=0.7107 Å) at 295K. The data was then collected using the co-step scan technique. The cell parameters were determined using all the valid reflections. The intensity data was corrected for Lorentz and polarization effects, and refinement was performed using the empirical absorption correction based on the equivalent reflections. The two structures were solved by direct methods and were refined by full-matrix least-squares data based on $F^2$. The non-hydrogen atoms were refined anisotopically, and the hydrogen atoms were included in an idealized geometry but not refined. Atomic scattering factors and anomalous dispersion factors were determined by the SHELX program.

(c) Calculation Methods and Input

In an attempt to understand structural features of the vanillin under investigation, all computations were carried out using the B3LYP method included in the Gaussian 03 package software together with the 6-31G* basis set function of the density functional theory (DFT). Carefully selected DFT methods applied with the 6-31* basis set were capable of reliable predicting the available experimental structure for the vanillin. The medium-sized 6-31G* basis set was usually considered sufficient for reliable optimization of geometries. The values of the three-dimensional coordinate obtained from the X-ray structural analysis were used as initial coordinates in the input to the calculation program. Therefore, the objective was to accurately calculate the properties of the vanillin.

(d) Geometry Optimizations

The results of the calculations were used to verify the reasonableness of the input coordinate data. If unreasonable data was used, either the geometric symmetry of the molecules would be destroyed or unusual bond length or bond angle would be produced. Any of these errors would result in the termination of the calculations. It was found that the calculations could achieve convergence much easier, if the input data was closer to the experimental values of the minimal energy points of the molecules. By starting the calculations with the coordinates of the X-ray structural analysis, the convergence of the DFT calculations was achieved in fewer steps. The converged calculations can then provide the optimal geometric bond lengths, bond angles and dihedral angles of the vanillin.

Result

Figure 2:
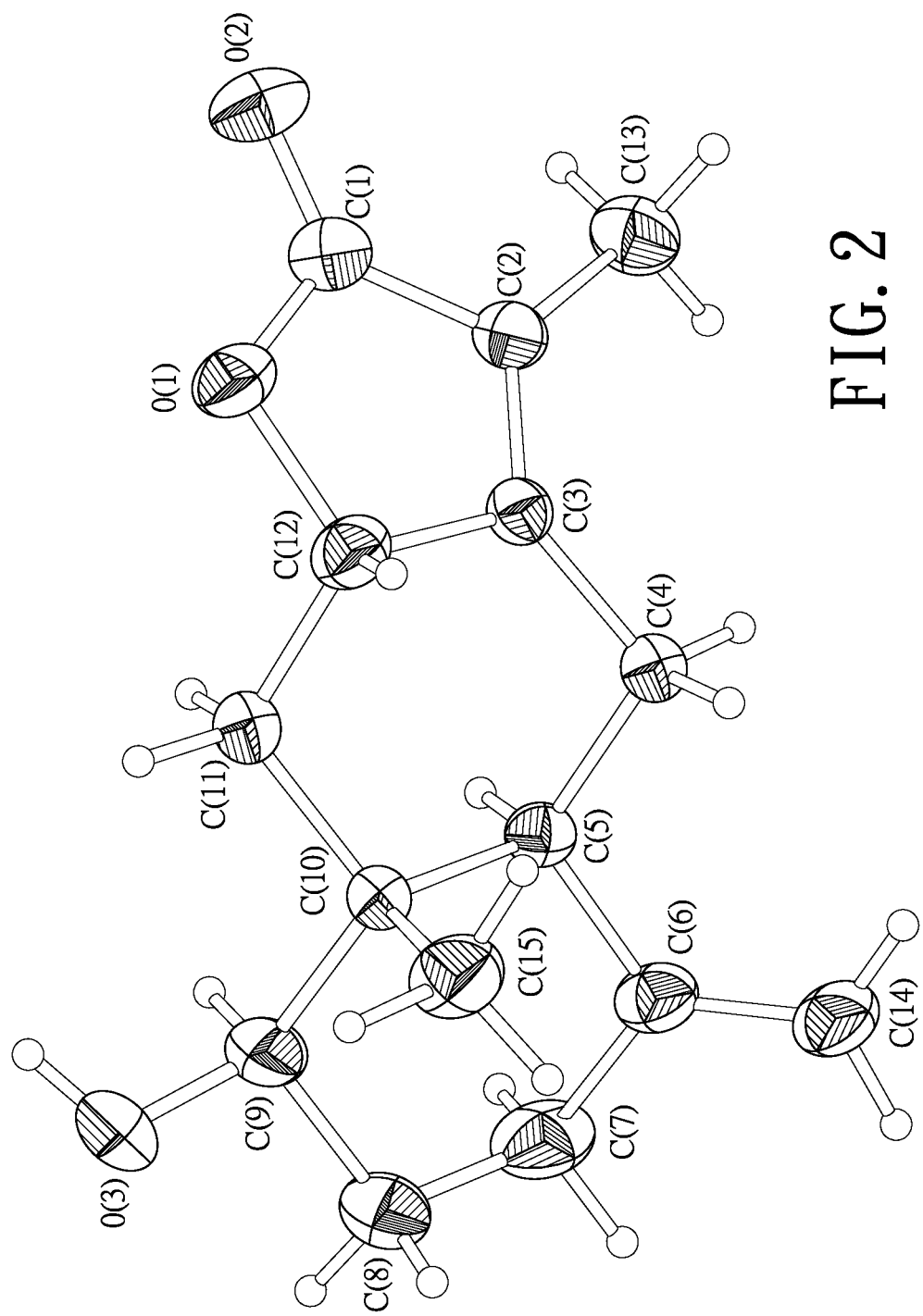
FIG. 2 is an ORTEP drawing of a neolitacumone B according to the present invention.
Figure 3:
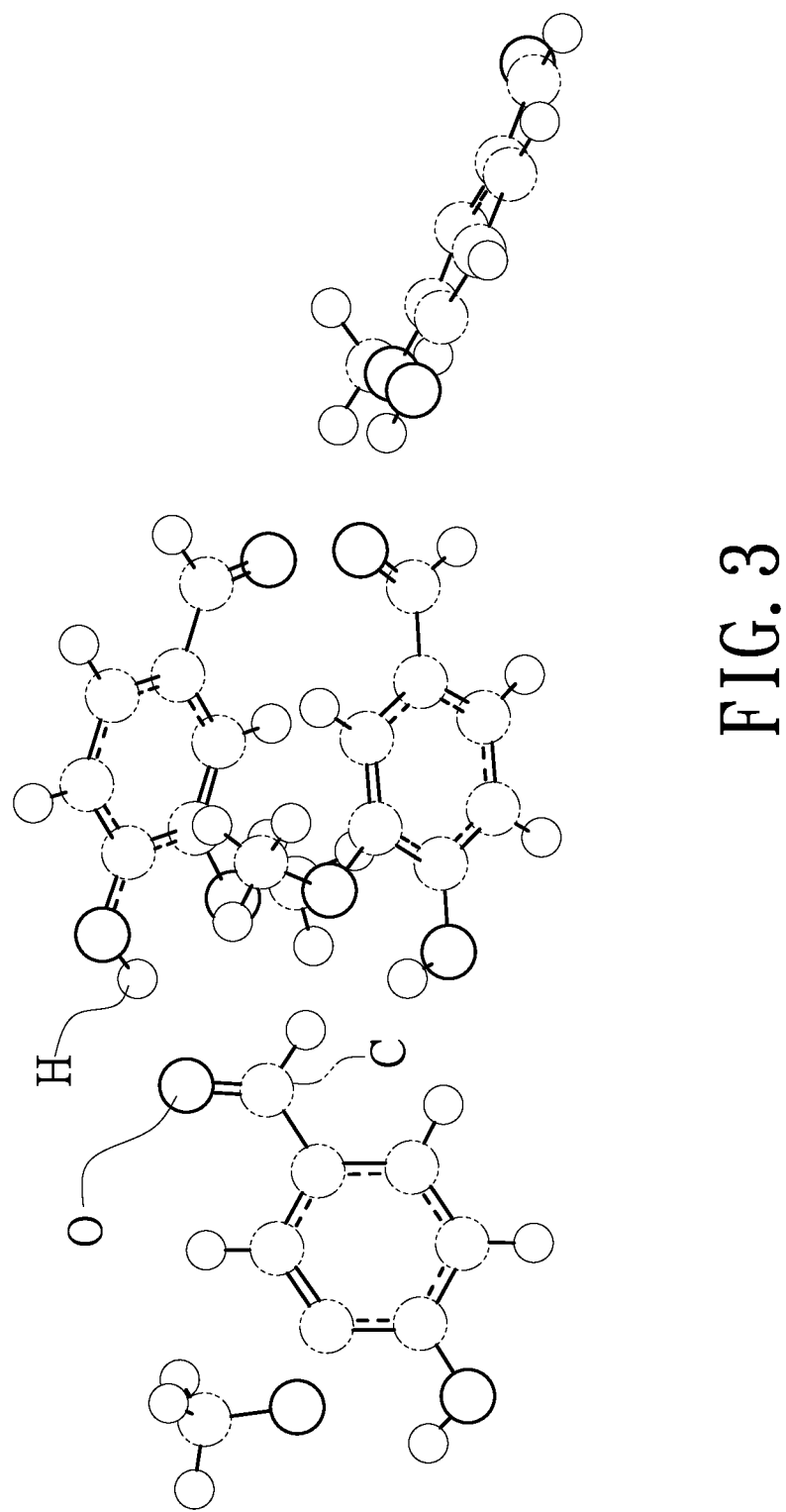
FIG. 3 is a DFT theoretical calculation diagram of the vanillin according to the present invention.

The structure of molecules plays an especially significant role in determining their chemical properties. A slight change in the structure of a biological molecule can completely destroy its usefulness to a cell or may even change the cell from a normal one to cancerous one. As a result, to search the geometric optimization of compound is particularly important. The obtained geometric structure of the vanillin was shown in formula (I) and formula (II). Through structural analysis using X-ray crystallography, the ORTEP diagrams of the vanillin molecules as shown in FIG. 1 and the neolitacumone B as shown in FIG. 2 were also identified. The values of the three-dimensional coordinate obtained from the X-ray structural analysis were used as initial coordinates in the input to the calculation program. As described earlier, the coordinates of the X-ray structural analysis are used as input data to compare the reliabilities and reasonableness of the theoretical methods used in this research. AM 1 semi-empirical method is first used to conduct calculations until convergence is achieved. The geometric optimization is then conducted using quantum chemical DFT modeling at the B3LYP/6-31G* level of theory has been carried out to investigate the vanillin. The DFT theoretical calculation diagram of the vanillin is shown in FIG. 3. Energies, in au, the predicted conformation of the vanillin is −2141.30629. Comparisons of theoretical and experimental data for bond lengths of the vanillin from the X-ray crystallography structural analysis and DFT calculations are shown in Tables 1.

TABLES 1 crystallographic data and optimized structure of natural product vanillin located using B3LYP/6-31G* calculations for atomic bond lengths (Å)

| Atomic bond lengths (Å) | Crystallographic data | B3LYP/6-31G* |
|---|---|---|
| O1-C1 | 1.339(3) | 1.360 |
| O2-C7 | 1.435(3) | 1.427 |
| O4-C9 | 1.342(3) | 1.341 |
| O5-C15 | 1.433(3) | 1.353 |
| O7-C17 | 1.345(3) | 1.544 |
| O8-C23 | 1.424(3) | 1.424 |
| O10-C25 | 1.348(3) | 1.344 |
| O11-C31 | 1.425(2) | 1.426 |
| C1-C6 | 1.375(3) | 1.392 |
| C2-C3 | 1.369(3) | 1.382 |
| C4-O5 | 1.372(3) | 1.399 |
| C5-C6 | 1.376(4) | 1.396 |
| C9-C10 | 1.408(3) | 1.423 |
| C11-C12 | 1.394(3) | 1.410 |
| C12-C16 | 1.461(4) | 1.465 |
| C17-C22 | 1.384(3) | 1.393 |
| C18-C19 | 1.374(3) | 1.381 |
| C20-C21 | 1.382(3) | 1.402 |
| C21-C22 | 1.371(4) | 1.393 |
| C25-C26 | 1.406(3) | 1.422 |
| C27-C28 | 1.383(3) | 1.410 |
| C28-C32 | 1.467(4) | 1.468 |
| O2-C2 | 1.356(5) | 1.369 |
| O3-C8 | 1.193(3) | 1.226 |
| O5-C10 | 1.350(3) | 1.552 |
| O6-C16 | 1.201(3) | 1.225 |
| O8-C18 | 1.361(3) | 1.370 |
| O9-C24 | 1.198(3) | 1.552 |
| O11-C26 | 1.361(3) | 1.368 |
| O12-C32 | 1.204(3) | 1.221 |
| C1-C2 | 1.405(3) | 1.417 |
| C3-C4 | 1.392(3) | 1.410 |
| C4-C8 | 1.462(3) | 1.466 |
| C9-C14 | 1.378(4) | 1.401 |
| C10-C11 | 1.371(3) | 1.383 |
| C12-C13 | 1.376(3) | 1.399 |
| C13-C14 | 1.396(4) | 1.392 |
| C17-C18 | 1.399(3) | 1.420 |
| C19-C20 | 1.394(3) | 1.412 |
| C20-C24 | 1.454(4) | 1.460 |

TABLES 1-continued crystallographic data and optimized structure of natural product vanillin located using B3LYP/6-31G* calculations for atomic bond lengths (Å)

| Atomic bond lengths (Å) | Crystallographic data | B3LYP/6-31G* |
|---|---|---|
| C25-C30 | 1.371(3) | 1.398 |
| C26-C27 | 1.368(3) | 1.384 |
| C28-C29 | 1.373(3) | 1.399 |
| C29-C30 | 1.379(4) | 1.392 |
| O3-H10A | 1.789 | 1.875 |
| O9-H4A | 1.766 | 1.818 |

The calculation of the vanillin that is in closest agreement with the experiment is also a molecule predicted by DFT calculations. In theoretical calculation analysis, four vanillin molecules (as shown in FIG. 2) of two intermolecular hydrogen bond lengths (O3-H10A and O9-H4A) were 1.875 Å and 1.818 Å, respectively. Locating the position of the hydrogen atom in the two intermolecular hydrogen bonds, they give unambiguous information on the existence and strength of the interaction. The density functional method calculations have shown that the two intermolecular hydrogen bonds significantly increase the structural stability. This increase in stability may be attributed to induction. The result is also in agreement with our X-ray experimental data which give hydrogen bond lengths 1.789 Å and 1.766 Å, respectively. This result is well established in predicting accuracy for two intermolecular hydrogen bonds involves four vanillin molecules. Table 2 provides the bond angles obtained from X-ray crystallography structural analysis and theoretical calculations.

TABLE 2

| Atomic torsion angle (°) | Crystallographic data | B3LYP/6-31G* |
|---|---|---|
| C2-O2-C7 | 117.1(2) | 118.0 |
| C10-O5-C15 | 117.1(2) | 117.7 |
| C18-O8-C23 | 117.6(2) | 118.0 |
| C26-O11-C31 | 116.9(2) | 118.0 |
| O1-C1-C6 | 118.6(2) | 120.6 |
| O1-C1-C2 | 122.1(2) | 118.9 |
| C6-C1-C2 | 119.3(2) | 120.5 |
| O2-C2-C3 | 126.3(2) | 126.9 |
| O2-C2-C1 | 114.1(2) | 113.1 |
| C3-C2-C1 | 119.7(2) | 114.2 |
| C2-C3-C4 | 120.6(2) | 119.5 |
| C5-C4-C3 | 119.2(2) | 120.2 |
| C5-C4-C8 | 119.9(2) | 120.2 |
| C3-C4-C8 | 120.9(2) | 119.6 |
| C4-C5-C6 | 120.9(2) | 120.4 |
| C1-C6-C5 | 120.3(2) | 119.3 |
| O3-C8-C4 | 126.9(2) | 123.9 |
| O4-C9-C14 | 118.9(2) | 118.6 |
| O4-C9-C10 | 121.4(2) | 122.3 |
| C14-C9-C10 | 119.7(2) | 119.1 |
| O5-C10-C11 | 126.8(2) | 125.5 |
| O5-C10-C9 | 114.0(2) | 114.4 |
| C11-C10-C9 | 119.2(2) | 120.1 |
| C10-C11-C12 | 120.3(2) | 120.3 |
| C13-C12-C11 | 120.1(2) | 119.7 |
| C13-C12-C16 | 119.4(2) | 120.8 |
| C11-C12-C16 | 120.6(2) | 119.5 |
| C14-C13-C12 | 120.0(2) | 120.2 |
| C13-C14-C9 | 120.7(2) | 120.5 |
| O6-C16-C12 | 126.3(3) | 124.4 |
| O7-C17-C22 | 118.6(2) | 120.1 |
| O7-C17-C18 | 121.7(4) | 119.6 |
| C22-C17-C18 | 119.7(2) | 120.3 |
| O8-C18-C19 | 126.1(2) | 126.7 |
| O8-C18-C17 | 114.1(2) | 113.1 |

TABLE 2-continued

| Atomic torsion angle (°) | Crystallographic data | B3LYP/6-31G* |
|---|---|---|
| C19-C18-C17 | 119.8(2) | 120.1 |
| C18-C19-C20 | 120.1(2) | 119.4 |
| C21-C20-C19 | 119.6(2) | 120.3 |
| C21-C20-C24 | 119.6(2) | 119.7 |
| C19-C20-C24 | 120.8(2) | 120.1 |
| C22-C21-C20 | 120.6(2) | 120.3 |
| C21-C22-C17 | 120.1(2) | 119.6 |
| O9-C24-C20 | 126.8(3) | 124.5 |
| O10-C25-C30 | 118.6(2) | 118.9 |
| O10-C25-C26 | 121.4(3) | 121.7 |
| C30-C25-C26 | 120.0(2) | 119.4 |
| O11-C26-C27 | 126.1(2) | 122.0 |
| O11-C26-C25 | 114.5(2) | 114.1 |
| C27-C26-C25 | 119.4(2) | 120.0 |
| C26-C27-C28 | 120.2(2) | 120.1 |
| C29-C28-C27 | 119.9(2) | 119.7 |
| C29-C28-C32 | 119.6(2) | 120.3 |
| C27-C28-C32 | 120.4(2) | 119.9 |
| C28-C29-C30 | 120.3(2) | 120.4 |
| C25-C30-C29 | 120.2(2) | 120.3 |
| O12-C32-C28 | 125.9(3) | 125.4 |

Table 3 provides the crystallographic data collected during this study. The overall B3LYP/6-31G* calculation of the molecular structures of the vanillin are in excellent agreement with experimental data.

TABLE 3 crystallographic data

| | Vanillin |
|---|---|
| Empirical formula | $C_8H_8O_3$ |
| Formula weight | 152.14 |
| Diffractometer used | BRUKER, SMART ApexCCD |
| T (K) | 295(2) |
| Wavelength | 0.71073 Å |
| Crystal system | Monoclinic |
| Space group | P2(1) |
| Unit cell dimensions | a = 14.0368(9) Å |
| | b = 7.8583(5) Å |
| | c = 14.9937(9) Å |
| | $\alpha$ = 90° |
| | $\beta$ = 115.446(1) ° |
| | $\gamma$ = 90° |
| Volume(Å$^3$) | 1493.19(16) |
| Z (atoms/unit cell) | 8 |
| $D_{calc}$ | 1.354 Mg/m$^3$ |
| Absorption coefficient | 0.104 mm$^{-1}$ |
| F (000) | 640 |
| Crystal size | 0.45 × 0.37 × 0.15 mm$^3$ |
| θrange for data collection | 1.50 to 27.50° |
| Index ranges | h (−18 to 18) |
| Index ranges | k (−10 to 10) |
| | l (−19 to 19) |
| Reflection collection | 15003 |
| Independent reflection | 6722(R(int) = 0.0302 |
| Completeness to θ = 27.50° | 100.0% |
| Absorption correction | Semi-empirical |
| Max. and min. transmission | 0.9845 and 0.9546 |
| Refinement method | Full-matrix least-squares on F$^2$ |
| Data/restraints/parameters | 6722/1/409 |
| GOF on F$^2$ | 1.106 |
| Final R indices [I>2σ(I)] | R1 = 0.0548 |
| | WR2 = 0.1103 |
| R indices (all data) | R1 = 0.0716 |
| | WR2 = 0.1194 |
| Absolute structure parameter | 1.4(9) |
| Largest diff. peak/hole [e Å$^{-3}$] | 0.139/−0.186 |

In summary, two intermolecular hydrogen bond lengths of four vanillin molecules are determined and are close to the experimental data of the X-ray crystallography. The result therefore reveals that the four vanillin molecules of two intermolecular hydrogen bonds in crystal structure are essential for formation of strong hydrogen bond. Moreover, it is shown that the intermolecular hydrogen bonding plays a determinant role in the conformational behavior of the molecules. These two intermolecular hydrogen bonds result in a high thermodynamic and structural stability. The calculations also show that the vanillin is all located at the stable, minimal point of the potential energy surface. Accordingly, the vanillin having tetramer structure was first identified herein. The result suggests that the tetramer structure may affect the ability of vanillin molecules passing through the cell membrane, which provides a different view of designing vanillin related drugs.

What is claimed is:

1. A vanillin having a tetramer structure, comprising a first monomer, a second monomer, a third monomer, a fourth monomer, a first intermolecular hydrogen bond between the first monomer and the fourth monomer, and a second intermolecular hydrogen bond between the second monomer and the third monomer; wherein each of the monomers is constituted by $C_8H_8O_3$.

2. The vanillin having a tetramer structure as claimed in claim 1, wherein the first intermolecular hydrogen bond is formed between an oxygen atom of a methoxy group of the first monomer and a hydrogen atom of a hydroxyl group of the fourth monomer, and the second intermolecular hydrogen bond is formed between an oxygen atom of a methoxy group of the third monomer and a hydrogen atom of a hydroxyl group of the second monomer.

3. The vanillin having a tetramer structure as claimed in claim 1, wherein the first intermolecular hydrogen bond has a bonding length of 1.875 Å, and the second intermolecular hydrogen bond has a bonding length of 1.818 Å.

4. The vanillin having a tetramer structure as claimed in claim 1, wherein the vanillin has characteristics of $^1$H NMR ($CDCl_3$) δ: 3.95 (3H, s, $C_3$—$OCH_3$), 6.20 (1H, br s, OH), 7.09 (1H, d, J=8.0 Hz, H-5), 7.30 (1H, d, J=2.0 Hz, H-2), 7.42 (1H, dd, J=8.0, 2.0 Hz, H-6), 9.76 (1H, s, CHO), and at 295 K, unit cell dimensions: a=14.0368(9) Å, b=7.8583(5) Å, c=14.9937(9) Å, α=90°, β=115.446(1)°, γ=90°, space group=P2(1), volume=1493.19(16) Å$^3$, Z=8, and $D_{calc}$=1.354 Mg/m$^3$.

* * * * *